United States Patent [19]
Wang et al.

[11] Patent Number: 5,209,102
[45] Date of Patent: May 11, 1993

[54] METHOD OF INTRODUCING AND CONTROLLING COMPRESSED GASES FOR IMPURITY ANALYSIS

[75] Inventors: Hwa-Chi Wang, Downers Grove; Richard J. Udischas, Chicago, both of Ill.

[73] Assignee: American Air Liquide, New York, N.Y.

[21] Appl. No.: 828,403

[22] Filed: Jan. 31, 1992

[51] Int. Cl.$^5$ .............................................. G01N 1/00
[52] U.S. Cl. ................................... 73/28.01; 73/31.03; 73/864.81
[58] Field of Search ................... 73/28.01, 23.2, 31.05, 73/31.03, 864.73, 864.81; 137/629, 630.16

Primary Examiner—Hezron E. Williams
Assistant Examiner—Michael Brock
Attorney, Agent, or Firm—Malcolm B. Wittenberg

[57] ABSTRACT

A system for analyzing particles from compressed gas. The system employs a back-filling technique to slowly balance the pressures on both sides of a control valve before operation. Use of a critical orifice as a flow control device for compressed gases of varying pressure is employed to provide a constant volumetric flow rate and thus a constant residence time within an impurity sensor.

12 Claims, 3 Drawing Sheets

FIG._1

METHOD OF INTRODUCING AND CONTROLLING COMPRESSED GASES FOR IMPURITY ANALYSIS

TECHNICAL FIELD OF THE INVENTION

The present invention involves a system and method of using it to allow for the precise analysis of particles found in compressed gases.

BACKGROUND OF THE INVENTION

There has long been a need to quantify particle concentration and to verify particle concentration in cylinder gases. While acceptable levels of particle content in cylinder gases continue to be assessed within SEMI and elsewhere, the predominant issue is the selection of an appropriate method for obtaining accurate, meaningful data.

Significant effort has been expended in establishing appropriate techniques for sampling particles from bulk gas pipelines for which particle specifications generally exist. However, the true particle content of compressed cylinder gases is more difficult to define for several reasons. Firstly, full cylinder pressure is typically 20 times greater than that of a pipeline, making pressure reduction for particle sampling a much more difficult task. Furthermore, the pressure in a gas cylinder, as opposed to a pipeline, decreases with usage which affects the detected particles in many ways. As a result, sampling techniques employed for pipeline gases are not directly applicable to cylinder gases. There are sampling artifacts associated with cylinder gas pressure reduction. For example, a pressure regulator which is universally employed is a source for small particles and a sink for large particles. The paper entitled *Factors Affecting Particle Content in High-Pressure Cylinder Gases* authored by Drs. Wang, Wen and Kasper of American Air Liquide taught the use of a particle analysis system for compressed cylinder gases which consisted of a means for pressure reduction followed by two particle counters in parallel. A laser particle counter model LAS-X from PMS and a condensation nucleus counter model 3760 from TSI were employed. However, there remained a number of practical obstacles which, prior to the present invention, prevented a straightforward, non-complex method of performing impurity analysis for compressed gases.

Recently, particle sensors capable of counting particles under a high pressure environment (up to 3,000 psi) became available (PMS-CGS, HIAC-ROYCO 5400). This eliminates the need for pressure reduction and its associated problems. However, using these instruments introduces the additional problem of gas introduction and flow control. Regarding gas introduction, direct introduction of cylinder gases into an impurity sensor involves an initial pressure pulse in the range of 100–3,000 psi. Contaminants generated by the initial pressure pulse often contaminate the impurity sensor and disable its operation. There is a need for a method to prevent the contamination caused by the initial pressure transient. On the subject of flow control, gas cylinders contain a limited amount of gas; cylinder pressure decreases with gas consumption. For a sensor requiring constant residence time, continuous adjustment of the mass flow controller is necessary to accommodate changes in cylinder pressure. There is a need for a device which maintains constant volumetric flow for gases of varying pressure.

Further, many impurity sensors require a constant residence time in the sensing volume of the instrument to make an accurate measurement. In other words, it requires a constant volumetric flow rate, independent of its operating pressure. Flow control for this type of sensor is trivial if the sensor is operated at a fixed pressure, since a simple conversion factor can be used to convert mass flow rate to volumetric flow rate. However, if the pressure of the gas sample varies with time, which is characteristic of cylinder gases, continuous adjustment is required for commonly used flow control devices such as mass flow controllers or rotameters.

It is thus an object of the present invention to provide a system to determine true particle content of compressed cylinder gases in a straightforward reducible and effective manner.

This and further objects of the present invention will be more readily appreciated when considering the following disclosure and appended drawings wherein:

FIGS. 1 and 2 represent schematic illustrations of systems useful in practicing the present invention; and FIG. 3 is a graph exhibiting the relationship between the number of false particle counts as a function of the time allotted for back-filling the system of the present invention.

SUMMARY OF THE INVENTION

The present invention involves a system for analyzing particles from compressed gas. This system includes a source of compressed gas, sensor means for measuring particle concentration within the gas and means to pressure balance the system.

The pressure balance component of the system comprises a first valve means located between said source of compressed gas and said sensor means, second valve means for introducing the gas to the system and filter means located downstream of the second valve means for similarly removing particle impurities in the source gas and/or introduced by the upstream components to allow a particle-free back-fill. A third valve means is located downstream of the filter means for controlling the exhaust of the gas from the system. A critical orifice is located between said filter means and sensor means for back-filling the gas to the sensor until there is a pressure equilibrium across the first valve means. The same critical orifice also provides a means for flow control during sampling.

The present invention further encompasses a method for employing the above-described system for analyzing particles from compressed gas.

DETAILED DESCRIPTION OF THE INVENTION

Figure 1:
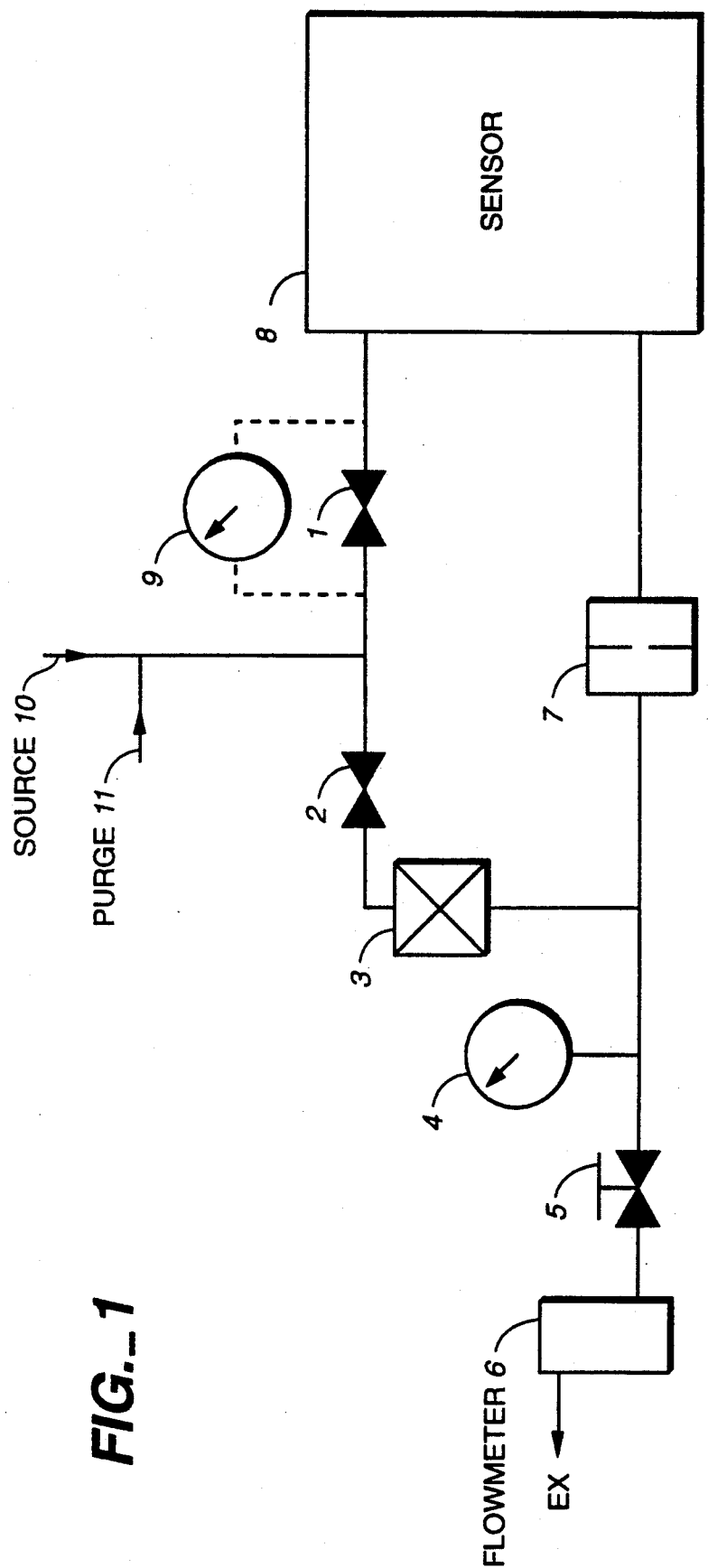
Figure 2:
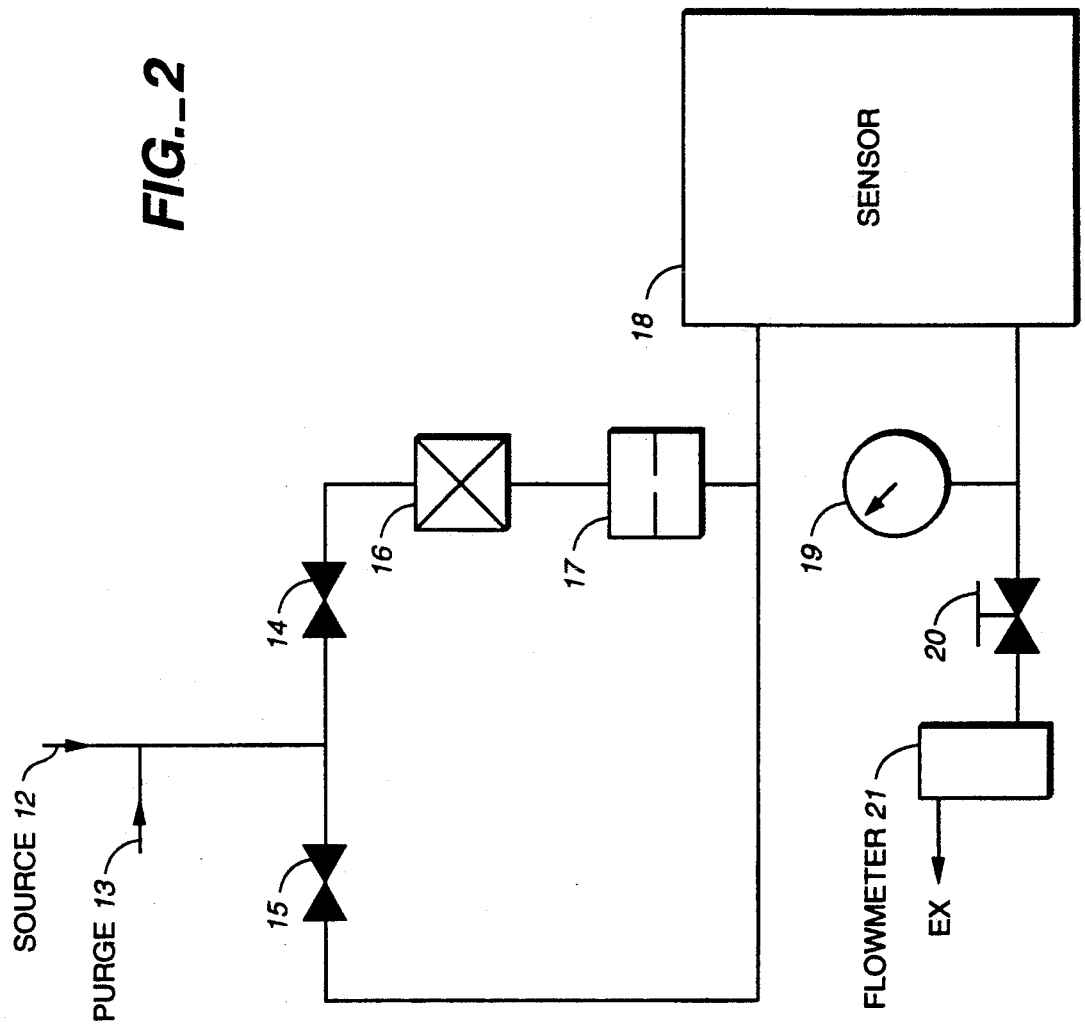

Referring to the appended drawings, FIGS. 1 and 2 illustrate two exemplary illustrations of configurations useful as systems for practicing the present invention. For sensors useful at low flow rates, up to a few hundred cc/min. at pressure, the arrangement shown in FIG. 1 is most appropriate wherein a common critical orifice is employed to control back-filling and sampling. By contrast, when employing sensors which require high flow rates the arrangement shown in FIG. 2 is most appropriate wherein a critical orifice is employed to control back-filling and a needle valve is employed to control the relatively large sampling flow rates.

Turning once again to FIG. 1, two operational modes are contemplated in employing such a system, i.e., the purge mode and sample mode. In the purge mode, two flow paths are available for a complete purge of the system. The first flow path includes valve 1, impurity sensor 8, orifice 7, pressure gauge 4, needle valve 5 and flow meter 6. The flow of the first path is controlled by orifice 7 and the volume of flow indicated by flowmeter 6.

The second flow path of FIG. 1 includes valve 2, filter 3, pressure gauge 4, needle valve 5 and flowmeter 6. The flow of the second path is controlled by needle valve 5, which usually is greater than the flow of the first path because the large surface area of filter 3 requires high purge flow.

It is contemplated that each flow path be first purged either sequentially or simultaneously by purge gas 11. Purge gases should be purified and filtered and comprise such inert gases as nitrogen, argon and helium.

It is contemplated that before gas sampling begins, pressure balance is established. In doing so, valve 1 which controls gas flow to the sensor is first closed. Source gas 10 at cylinder pressure is introduced to the back-filling leg. It is noted that because of the closure of valve 1, the sensor is isolated from pressure surges introduced by cylinder source gas 10 as well as contaminants introduced by valve 2 as filter 3 is employed downstream of valve 2.

After the pressure balance stage, the majority of flow of the source gas is exhausted from the system at a flow rate which is controlled by needle valve 5. This flow rate is indicated by flow meter 6 which can be, for example, a mass flowmeter or rotameter. Pressure gauge 4, upstream of needle valve 5, provides the user with the pressure of source gas 10.

During the pressure balancing process, flow of source gas 10 is caused to pass through critical orifice 7 to back-fill the sampling leg. Back-filling continues until the pressures on both sides of control valve 1 are balanced. The time required to reach pressure balance can be determined either by direct measurement or by calculation. Direct measurement is accomplished by employing differential pressure gauge 9 located across control valve 1. However, the installation of a differential pressure gauge introduces dead spaces just before the sensor which require a dedicated procedure to purge. Alternatively, one can estimate the time required to reach pressure balance by the semi-empirical equation $$t = F \frac{V\sqrt{T}}{D^2 GC} \quad (1)$$

wherein:
t = the time required for back-fill in minutes
F = 1.5 is the empirical constant,
V = the total internal volume in cc between critical orifice 7 and control valve 1,
T = the temperature in Kelvin,
D = the orifice diameter in μm
C = the discharge coefficient between 0.8 and 1.0 depending upon the individual orifice, and
G = the gas parameter defined as, $$G = \left[\frac{K}{M}\right]^{0.5} \left[\frac{2}{K+1}\right]^{\frac{K+1}{2K-2}} \quad (2)$$

wherein K and M are the heat capacity ratio and molecular weight in g/mole of the gas, respectively. The time allotted for back-filling should be greater than the calculated value from the above equation.

After pressure balance is reached by back-filling, sampling can be started by opening control valve 1 for the sampling leg and closing control valve 2 for the back-fill leg. Flow of source gas 10 is now directed through sensor 8 at the same pressure as the source gas and flow is controlled by critical orifice 7. As a preferred embodiment, the critical orifice can be used to control sampling flow through the sensor. The diameter of the orifice is determined by the specific residence time of the sensor as follows:

$$D = \left[\frac{\sqrt{T}}{1.28 CG} \frac{V_S}{t_S}\right]^{0.5} \quad (3)$$

wherein:
$V_s$ = the internal volume of the sensor in cc, and
$t_s$ = the specific residence time of the sensor in minutes.
It should be noted that the above-recited relationship is not dependent upon gas pressure. In other words, one single orifice diameter can be used for a given sensor even if the pressure of the source gas is changing with time.

The actual flow rate of source gas 10 passing through sensor 8 will obviously decrease with decreasing pressure. The flow rate at any particular time can be determined simply by referencing flowmeter 6. The total sample volume can be easily obtained by integrating the indicated flow rate over the sampling period. If a flowmeter is not available, total sample volume can be calculated by the following equation $$V_T = 2.61 \frac{D^2 GC}{\sqrt{T}} (P_i + P_f)s \quad (4)$$

wherein:
$V_T$ = the total sample volume in cc,
$P_i$ and $P_f$ = the initial and final pressure in psia, and
s = the sampling interval in seconds As noted previously, FIG. 2 is yet another configuration of the present system which is optimally employed with higher flow rates from source gas 12.

Once again, FIG. 2 provides for both a purge mode and sample mode. In the purge mode two flow paths are available for a complete purge of the system. The first flow path includes valve 15, impurity sensor 18, pressure gauge 19, needle valve 20 and flowmeter 21. The flow of the second path, includes valve means 14, filter 16, critical orifice 17, sensor 18, pressure gauge 19, needle valve 20 and flowmeter 21.

As in the prior example, both flow paths can be purged sequentially or simultaneously with purge gas 13 which can be, for example, nitrogen, argon or helium.

In pressure balancing the system of FIG. 2, first valve means 15 is closed. As such, source gas 12 at cylinder pressure is introduced to the back-filling leg through second valve means 14. Contaminants introduced by valve 14 are removed by filter 16 downstream of the valve. Large pressure surges are prevented from adversely affecting sensor 18 for source gas 12 must pass through critical orifice 17 prior to reaching sensor 18. The pressure of source gas 12 passing through critical orifice 17 and sensor 18 can be determined by reference to flowmeter 21.

As gas from source 12 passes through critical orifice 17, the sampling leg is back filled. This condition continues until pressures on both sides of valve means 15 are balanced. As with the case regarding the system of FIG. 1, the time required to reach pressure balance can be determined either by direct measure or calculation. Direct measurement is accomplished by a differential pressure gauge (not shown) across first valve means 15. However, installation of the deferential pressure gauge introduces dead spaces just before the sensor which require a dedicated procedure to purge. An alternative method is to estimate the time required to reach pressure balance by semi-empirical equation (1).

After pressure balance is achieved by back-filling, sampling can be started by opening first valve means 15 and closing second valve means 14. The flow is now directed through sensor 18 at the same pressure as the source gas and the flow of source gas 12 can be controlled by needle valve 20 and observed by flowmeter 21. Unlike the system of FIG. 1, however, flow of source gas 12 is not directed through orifice 17 after pressure balance across first valve means 15 has been accomplished.

Figure 3:
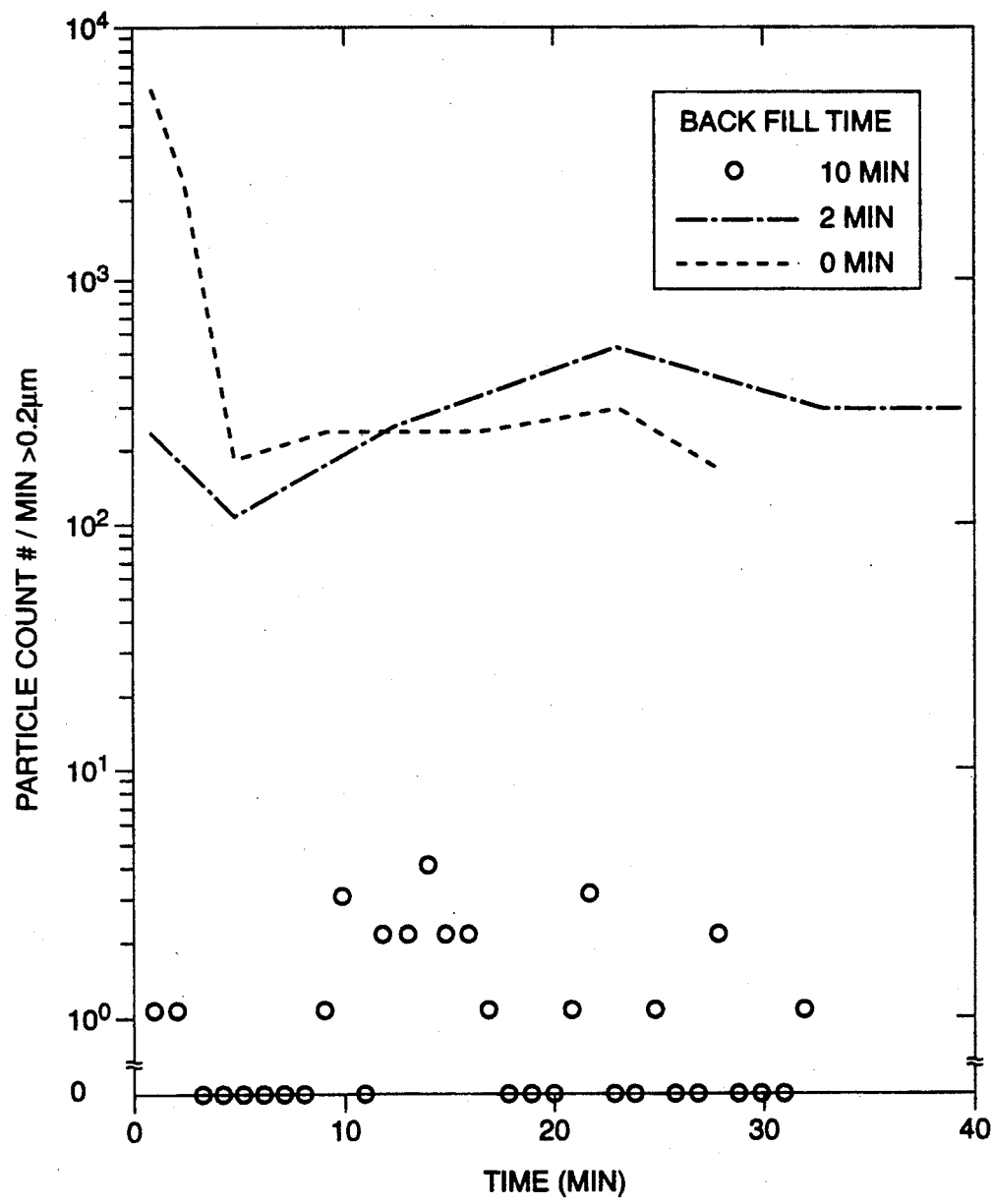

The benefits achieved through effective back-filling have been confirmed in reference to FIG. 3. A high pressure particle sensor (PMS-CGS) was connected to a flow control system similar to FIG. 1. When no back-filling was carried out, particles generated by the initial pressure pulse were observed to contaminate the particle sensor and yield fairly high false counts. When back-filling was carried out for two minutes, the initial particle counts decreased but the problem of sensor contamination remained. By contrast, when back-filling was allowed to take place for 10 minutes and, as a result, pressure balance was achieved, true particle counts were obtained which were at least two orders of magnitude smaller than false counts.

We claim:

1. A system for analyzing particles from compressed gas, said system comprising a sensor means for measuring said particle impurity within said gas, means to pressure balance said system comprising first valve means located between a source of compressed gas and said sensor means, second valve means for introducing said gas to said system, filter means located downstream of said second valve means for substantially removing particle impurities in the source gas and/or introduced by the upstream components, a third valve means located downstream of said filter means for controlling the exhaust of the gas from the system, a critical orifice located between said filter means and sensor means for back-filling said gas to said sensor until there is a pressure equilibrium across said first valve means.

2. The system of claim 1 further including a differential pressure gauge located across said first valve means for determining when gas pressure has been equalized across said first valve means and thus the back filling of said gas to said sensor has been completed.

3. The system of claim 1 further including a flow meter located downstream of said third valve means.

4. The system of claim 1 wherein the diameter of said critical orifice is determined by the following equation:

$$D = \left[ \frac{\sqrt{T}}{1.28CG} \frac{V_s}{t_s} \right]^{0.5}$$

wherein:
D = the orifice diameter in $\mu m$,
C = the discharge coefficient between 0.8 and 1.0 depending on the individual orifice, and
G = the gas parameter defined as $$G = \left[ \frac{K}{M} \right]^{0.5} \left[ \frac{2}{K+1} \right]^{\frac{K+1}{2K-2}}$$

wherein:
K and M = the heat capacity ratio and the molecular weight of the gas, respectively,
$V_s$ = the internal volume of the sensor,
T = the temperature in Kelvin, and
$t_s$ = the specific residence time of the sensor.

5. The system of claim 1 further including a source of purge gas located upstream of said first and second valve means.

6. The system of claim 5 wherein said purge gas is a member selected from the group consisting of $N_2$, Ar, and He.

7. A method for analyzing compressed gas for particle concentrations comprising introducing a source of compressed gas into a system, said system comprising a sensor means for measuring particle concentration within the gas, means to pressure balance the system which comprises first valve means located between said source of compressed gas and said sensor means, second valve means for introducing said gas to said system, filter means located downstream of said second valve means for substantially removing particle impurities in the source gas and/or introduced by the upstream components, third valve means located downstream of said filter means for controlling the exhaust of said gas from said system, and a critical orifice located between said filter means and sensor means for back-filling said gas to said sensor until there is a pressure equilibrium across said first valve means, said method comprising introducing said compressed gas while said first valve means is closed, causing said compressed gas to pass through said second valve means, filter means and critical orifice for a length of time sufficient to equalize pressure across said first valve means while said third valve means is closed and opening said first valve means and third means once pressure across said first valve means has been equalized enabling said compressed gas to pass through said sensor means and critical orifice prior to being expelled from said system through said third valve means.

8. The method of claim 7 wherein a purge gas is first introduced to said system prior to or simultaneous with the initial introduction of said compressed gas.

9. The method of claim 8 wherein said purged gas is a member selected from the group consisting of $N_2$, Ar and He.

10. The method of claim 7 wherein the diameter of said critical orifice is determined by the following equation:

$$D = \left[ \frac{\sqrt{T}}{1.28CG} \frac{V_S}{t_S} \right]^{0.5}$$

wherein:
D = the orifice diameter in μm,
C = the discharge coefficient between 0.8 and 1.0 depending on the individual orifice, and
G = the gas parameter defined as $$G = \left[ \frac{K}{M} \right]^{0.5} \left[ \frac{2}{K+1} \right]^{\frac{K+1}{2K-2}}$$

wherein:
K and M = the heat capacity ratio and the molecular weight of the gas, respectively,
$V_s$ = the internal volume of the sensor,
T = the temperature in Kelvin, and
$t_s$ = the specific residence time of the sensor.

11. The method of claim 7 wherein the time required to reach pressure balance of the system is estimated by the semi-empirical equation $$t = F \frac{V\sqrt{T}}{D^2 GC}$$

wherein:
t = the time required for back-fill in minutes
F = 1.5 is the empirical constant,
V = the total internal volume in cc between critical orifice and control valve,
T = the temperature in Kelvin,
D = the orifice diameter in μm
C = the discharge coefficient between 0.8 and 1.0 depending upon the individual orifice, and
G = the gas parameter defined as, $$G = \left[ \frac{K}{M} \right]^{0.5} \left[ \frac{2}{K+1} \right]^{\frac{K+1}{2K-2}}$$

wherein:
K and M = the heat capacity ratio and the molecular weight of the gas, respectively.

12. The method of claim 7 wherein said critical orifice is employed to control sampling flow through the sensor.

* * * * *